US012156659B2

(12) United States Patent
Lin et al.

(10) Patent No.: US 12,156,659 B2
(45) Date of Patent: Dec. 3, 2024

(54) INTRAORAL VERTICAL RAMUS OSTEOTOMY SURGICAL GUIDES

(71) Applicant: VANDERBILT UNIVERSITY, Nashville, TN (US)

(72) Inventors: Susie I Ching Lin, Nashville, TN (US); Kevin C Galloway, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 302 days.

(21) Appl. No.: 17/580,977

(22) Filed: Jan. 21, 2022

(65) Prior Publication Data
US 2022/0233202 A1    Jul. 28, 2022

Related U.S. Application Data

(60) Provisional application No. 63/140,274, filed on Jan. 22, 2021.

(51) Int. Cl.
*A61B 17/17* (2006.01)
*A61B 17/15* (2006.01)
*A61C 1/08* (2006.01)
*A61B 17/56* (2006.01)
*A61B 90/00* (2016.01)

(52) U.S. Cl.
CPC ............ *A61B 17/176* (2013.01); *A61B 17/15* (2013.01); *A61B 17/151* (2013.01); *A61C 1/084* (2013.01); *A61B 2017/568* (2013.01); *A61B 2090/061* (2016.02)

(58) Field of Classification Search
CPC ............ A61B 17/151; A61B 2017/568; A61B 2090/061
See application file for complete search history.

(56) References Cited

U.S. PATENT DOCUMENTS

| | | | | |
|---|---|---|---|---|
| 3,664,022 A | * | 5/1972 | Small | A61C 1/084 433/174 |
| 4,524,766 A | * | 6/1985 | Petersen | A61B 17/1675 606/88 |
| 2004/0097927 A1 | * | 5/2004 | Yeung | A61B 17/1757 606/279 |
| 2013/0096680 A1 | * | 4/2013 | Ribeiro | A61F 2/4644 606/88 |

* cited by examiner

*Primary Examiner* — Sameh R Boles
(74) *Attorney, Agent, or Firm* — Thomas| Horstemeyer, LLP

(57) ABSTRACT

Provided herein is an IVRO surgical guide for positioning a cutting guide on a mandibular ramus such that the mandibular ramus is clamped between a hooked distal end and a slidable component having a curved claw. The cutting guide is placed at a predetermined distance from the posterior edge of the ramus at the mid-waistline of the mandibular ramus along a curvilinear shaft in contact with the lateral surface of the ramus. The cutting guide can accommodate a saw for performing the osteotomy.

8 Claims, 15 Drawing Sheets

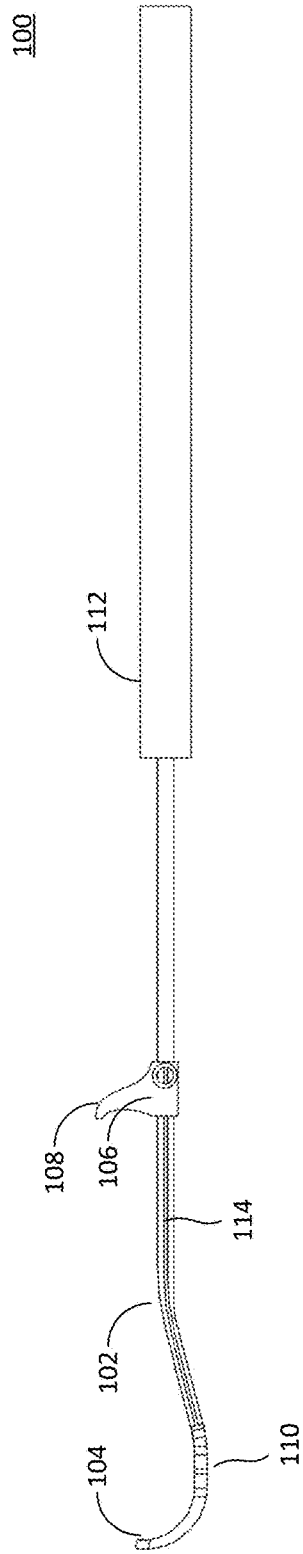
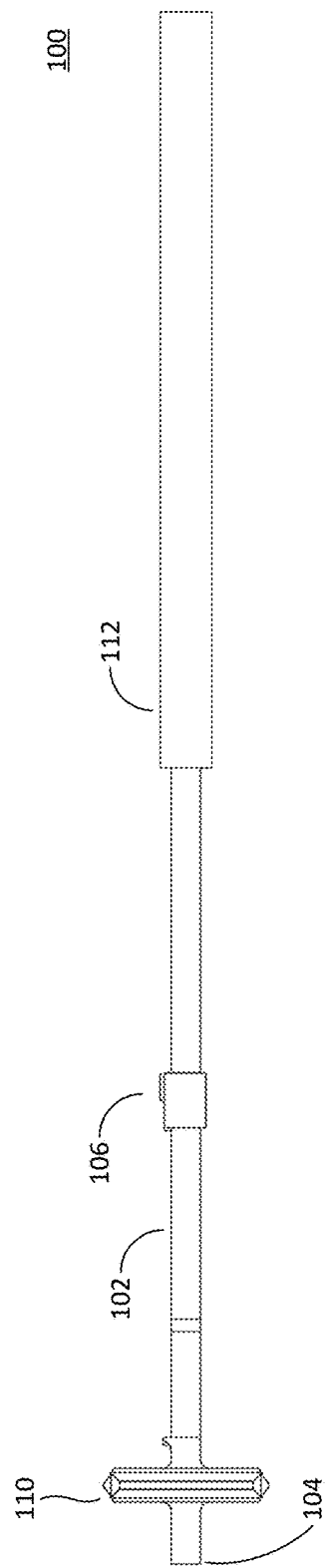
Fig. 1A
Fig. 1B

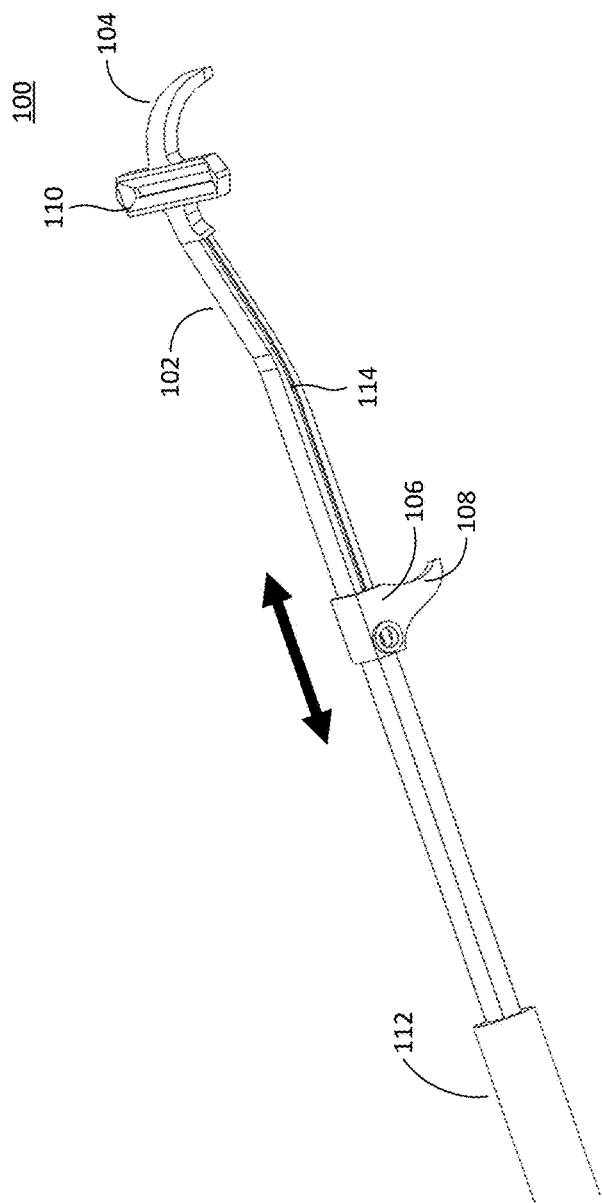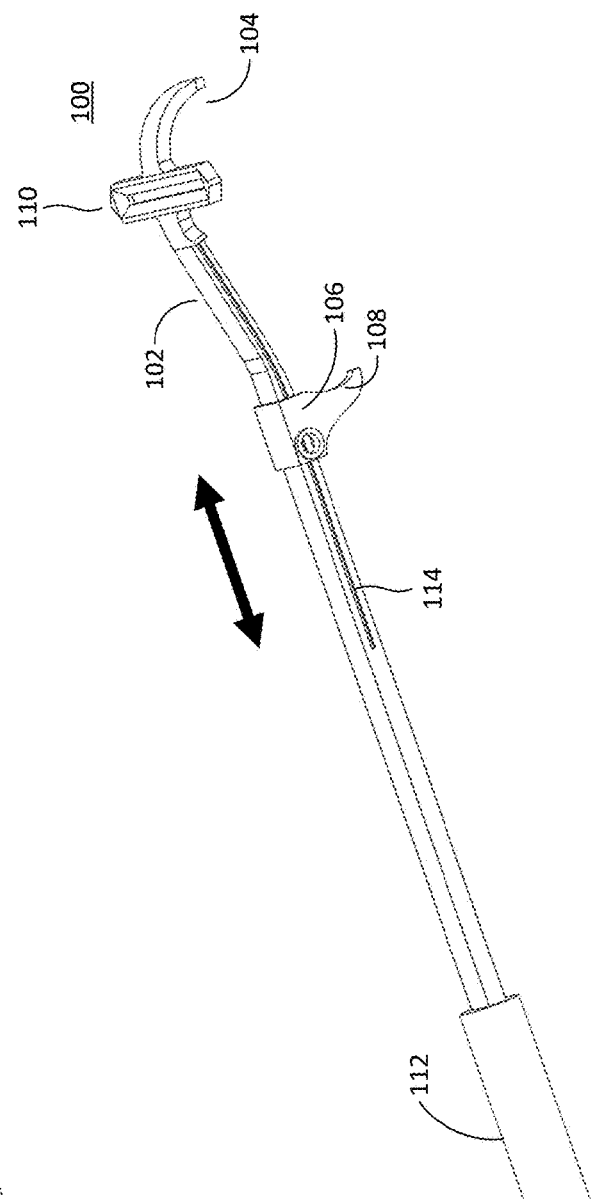

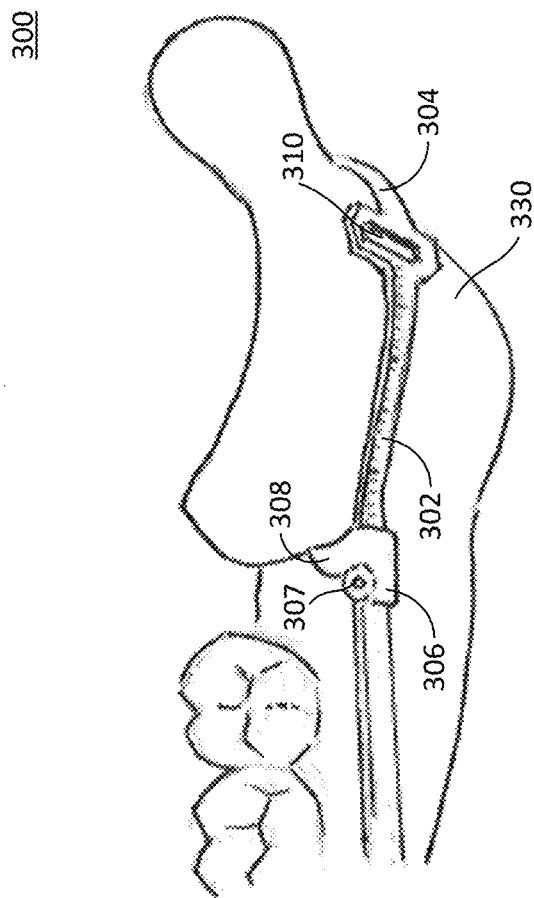
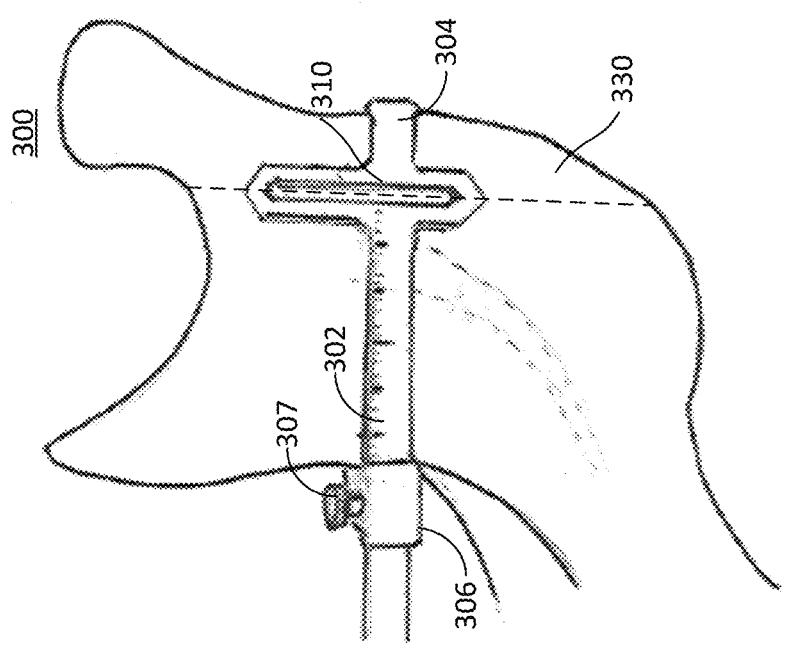
Fig. 3B
Fig. 3A

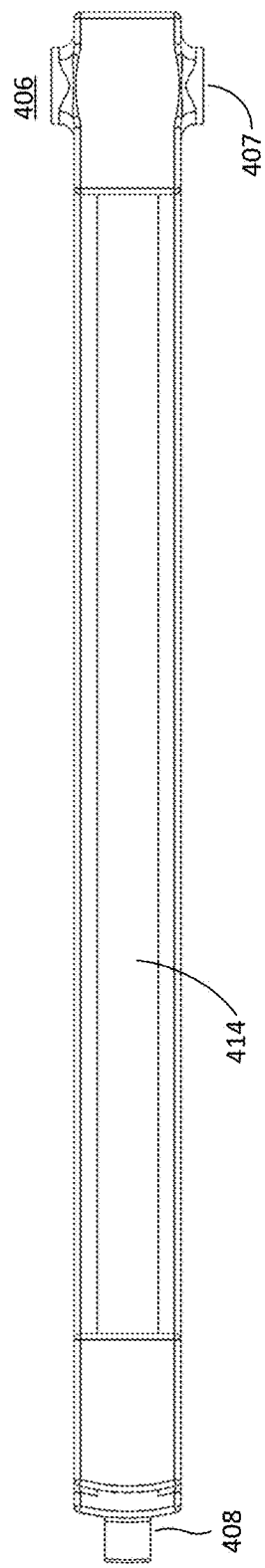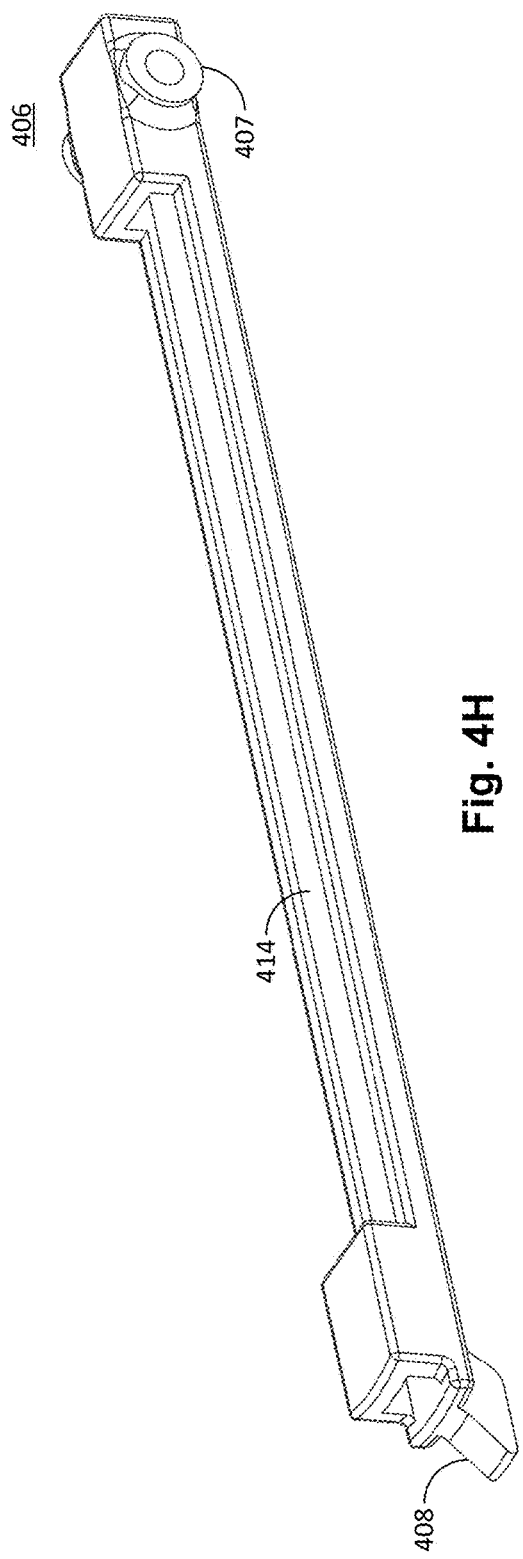

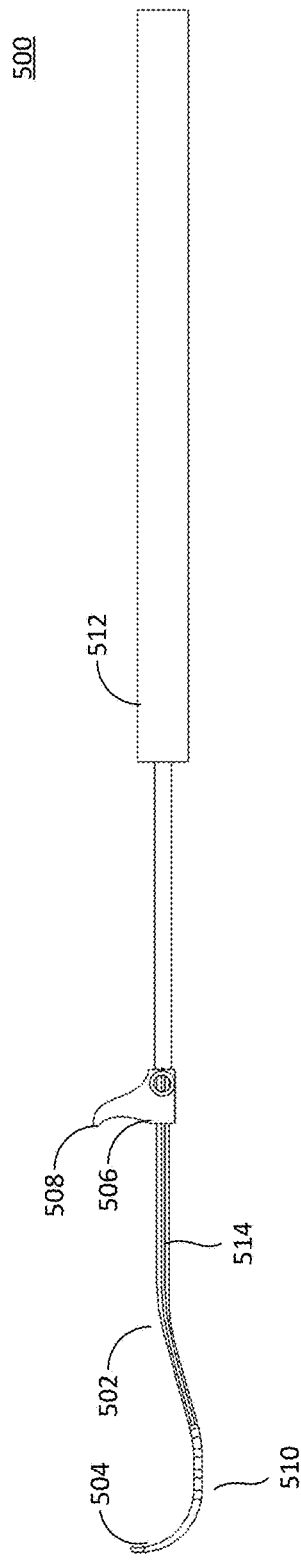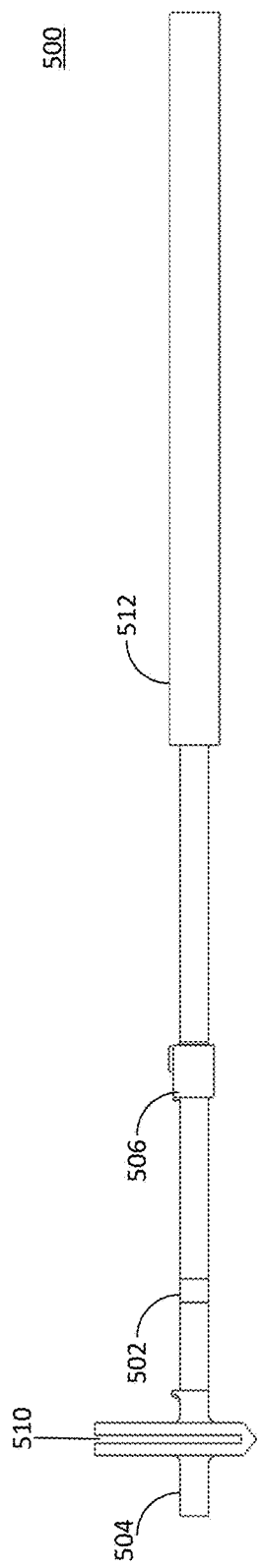
Fig. 5A
Fig. 5B

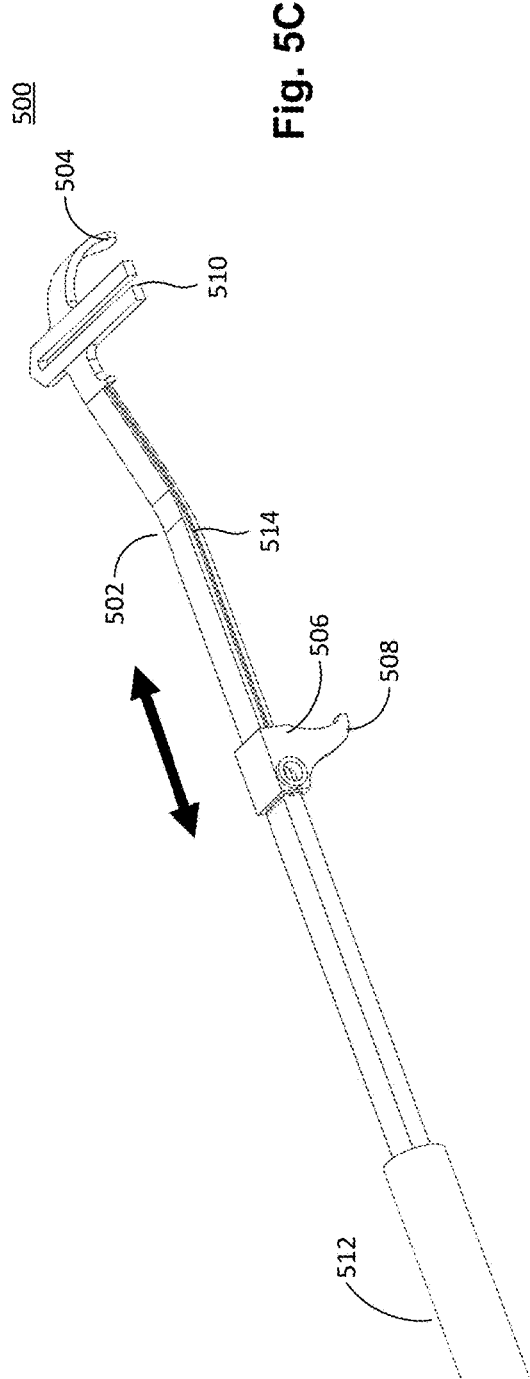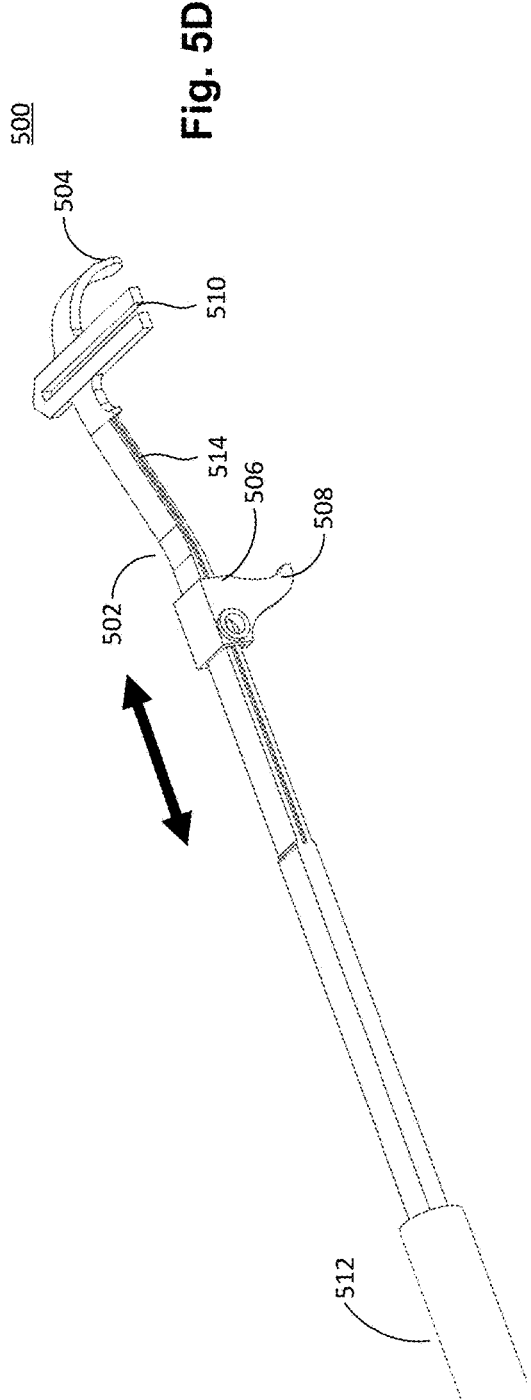

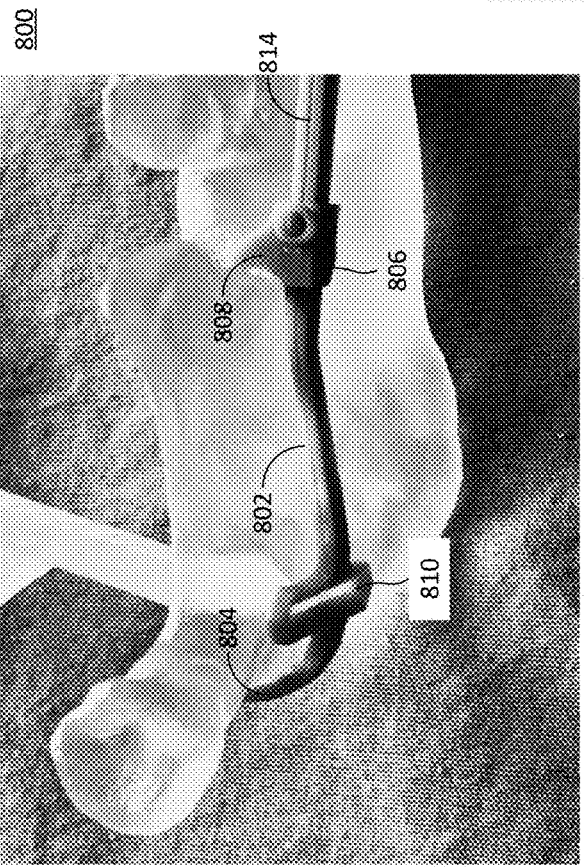
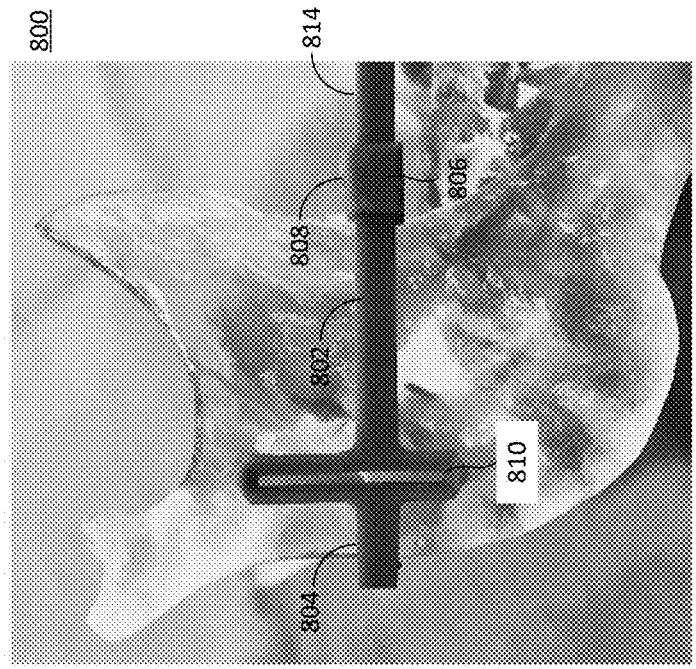
Fig. 8A
Fig. 8B

INTRAORAL VERTICAL RAMUS OSTEOTOMY SURGICAL GUIDES

CROSS-REFERENCE TO RELATED APPLICATIONS

This application claims the benefit of and priority to U.S. Provisional Application Ser. No. 63/140,274, having the title "INTRAORAL VERTICAL RAMUS OSTEOTOMY SURGICAL GUIDES", filed on Jan. 22, 2021, the disclosure of which is incorporated herein by reference in its entirety.

BACKGROUND

The intraoral vertical ramus osteotomy (IVRO) is a relatively simple, but useful technique with many applications, including management of horizontal mandibular excess, mandibular asymmetry and correction of minor mandibular deficiency. Modified condylotomy is a variation of the IVRO with partial stripping of the medial pterygoid attachment from the proximal segment to achieve the desired condylar sag and increased jaw joint space. Increasing joint space frequently promotes disc reduction in joints with articular disc displacement with reduction or recent progression to disc displacement without reduction; improves pain even if disc position remains unchanged; and seems to favorably alter the natural course of internal derangement.

Some of the intraoperative challenges typically associated with IVRO include limited visualization and difficulty judging the position of the lingua. Incorrect osteotomy techniques can lead to inadequate proximal segment medial pterygoid attachment, inferior alveolar nerve damage, and/or vascular injury of the inferior alveolar, masseteric, maxillary arteries or retromandibular vein.

SUMMARY

Embodiments of the present disclosure provide for apparatuses and methods for performing intraoral vertical ramus osteotomy (IVRO).

An embodiment of the present disclosure includes an IVRO surgical guide that can include a curvilinear shaft comprising a hooked distal end and a cutting guide. The device also includes a slidable component that slidably engages with the curvilinear shaft proximal to the cutting guide. The slidable component can include a curved claw.

An embodiment of the present disclosure also includes a method for performing intraoral vertical ramus osteotomy that includes engaging a hooked distal end of an IVRO as above around the mid-posterior mandibular ramus of a patient such that a curvilinear shaft of the device is in contact with a lateral surface of the mandibular ramus. A slidable component is moved along the curvilinear shaft until a curved claw of the slidable component contacts the mid-anterior mandibular ramus such that the mandibular ramus is clamped between the hooked distal end and the slidable component, and wherein the curvilinear shaft is positioned along a mid-waistline of the mandibular ramus when the IVRO surgical guide is in the clamped position. The device includes a cutting guide located on the curvilinear shaft at a predetermined distance from the hooked distal end.

Other compositions, apparatus, methods, features, and advantages will be or become apparent to one with skill in the art upon examination of the following drawings and detailed description. It is intended that all such additional compositions, apparatus, methods, features and advantages be included within this description, be within the scope of the present disclosure, and be protected by the accompanying claims.

BRIEF DESCRIPTION OF THE DRAWINGS

Further aspects of the present disclosure will be more readily appreciated upon review of the detailed description of its various embodiments, described below, when taken in conjunction with the accompanying drawings.

FIGS. 1A-1F provide various views of an IVRO surgical guide in accordance with embodiments of the present disclosure. The curved claw of the sliding component engages the mid-anterior ramus. FIG. 1A presents a top view; FIG. 1B presents a front view; FIGS. 1C and 1D illustrate the adjustable sliding component from a perspective view. FIG. 1E presents various views of the sliding component (left side perspective, front, and right side respectively); and FIG. 1F presents a prototype of the IVRO surgical guide with the cutting slot placed 8 mm from the posterior ramus (shown on calipers).

FIG. 3A provides a lateral view of an IVRO surgical guide on a left mandibular ramus with the distal tip engaging the mid-posterior ramus and the curved claw of the sliding component engaging the mid-anterior ramus in accordance with embodiments of the present disclosure. FIG. 3B provides a top perspective view of the surgical guide shown in FIG. 2A on a left mandibular ramus.

FIGS. 4A-4H provide various views of an IVRO surgical guide having the curved claw as part of the handle, and wherein the handle slides to adjust the device to the patient. FIG. 4A provides an exploded perspective view of an IVRO surgical guide with a curved claw and locking mechanism adapted to the handle in accordance with embodiments of the present disclosure. FIG. 4B provides an assembled perspective view of an IVRO surgical guide with the curved claw and locking mechanism adapted to the handle in accordance with embodiments of the present disclosure. FIGS. 4C-4E illustrate the sliding handle in the open and clamped positions. FIGS. 4F-4H provide various views of the sliding handle.

FIGS. 5A-5D provide various views of an IVRO surgical guide in accordance with embodiments of the present disclosure. The curved claw of the sliding component engages the mid-anterior ramus. In this embodiment, the cutting slot is open-ended. FIG. 5A presents a top view; FIG. 5B presents a front view; FIGS. 5C and 5D illustrate the adjustable sliding component from a perspective view.

FIG. 6A shows the cutting slot in the default position.

FIG. 6B shows the sliding mechanism, allowing for the cutting slot to be positioned by the surgeon.

FIGS. 8A-8B are camera images of a prototype IVRO surgical guide fitted to a 3D-printed right mandibular ramus in accordance with embodiments of the present disclosure.

Figure 1E:
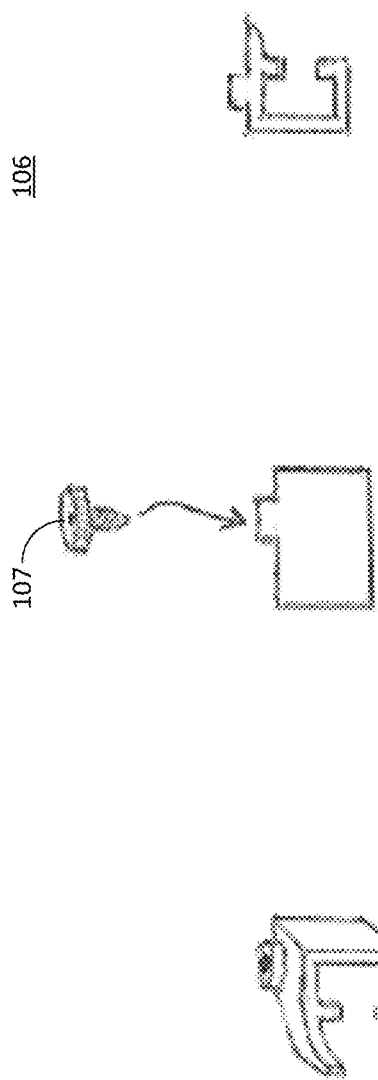

The drawings illustrate only example embodiments and are therefore not to be considered limiting of the scope described herein, as other equally effective embodiments are within the scope and spirit of this disclosure. The elements and features shown in the drawings are not necessarily drawn to scale, emphasis instead being placed upon clearly illustrating the principles of the embodiments. Additionally, certain dimensions may be exaggerated to help visually convey certain principles. In the drawings, similar reference numerals between figures designate like or corresponding, but not necessarily the same, elements.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

The foregoing and other features and advantages of various aspects of the invention(s) will be apparent from the following, more-particular description of various concepts and specific embodiments within the broader bounds of the invention(s). Various aspects of the subject matter introduced above and discussed in greater detail below may be implemented in any of numerous ways, as the subject matter is not limited to any particular manner of implementation. Examples of specific implementations and applications are provided primarily for illustrative purposes.

Unless otherwise defined, used or characterized herein, terms that are used herein (including technical and scientific terms) are to be interpreted as having a meaning that is consistent with their accepted meaning in the context of the relevant art and are not to be interpreted in an idealized or overly formal sense unless expressly so defined herein. For example, if a particular composition is referenced, the composition may be substantially, though not perfectly pure, as practical and imperfect realities may apply; e.g., the potential presence of at least trace impurities (e.g., at less than 1 or 2%) can be understood as being within the scope of the description; likewise, if a particular shape is referenced, the shape is intended to include imperfect variations from ideal shapes, e.g., due to manufacturing tolerances. Percentages or concentrations expressed herein can represent either by weight or by volume.

Although the terms, first, second, third, etc., may be used herein to describe various elements, these elements are not to be limited by these terms. These terms are simply used to distinguish one element from another. Thus, a first element, discussed below, could be termed a second element without departing from the teachings of the exemplary embodiments.

Spatially relative terms, such as "above," "below," "left," "right," "in front," "behind," and the like, may be used herein for ease of description to describe the relationship of one element to another element, as illustrated in the figures. It will be understood that the spatially relative terms, as well as the illustrated configurations, are intended to encompass different orientations of the apparatus in use or operation in addition to the orientations described herein and depicted in the figures. For example, if the apparatus in the figures is turned over, elements described as "below" or "beneath" other elements or features would then be oriented "above" the other elements or features. Thus, the exemplary term, "above," may encompass both an orientation of above and below. The apparatus may be otherwise oriented (e.g., rotated 90 degrees or at other orientations) and the spatially relative descriptors used herein interpreted accordingly.

Further still, in this disclosure, when an element is referred to as being "on," "connected to," "coupled to," "in contact with," etc., another element, it may be directly on, connected to, coupled to, or in contact with the other element or intervening elements may be present unless otherwise specified.

The terminology used herein is for the purpose of describing particular embodiments and is not intended to be limiting of exemplary embodiments. As used herein, singular forms, such as "a" and "an," are intended to include the plural forms as well, unless the context indicates otherwise. Additionally, the terms, "includes," "including," "comprises" and "comprising," specify the presence of the stated elements or steps but do not preclude the presence or addition of one or more other elements or steps.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Before the embodiments of the present disclosure are described in detail, it is to be understood that, unless otherwise indicated, the present disclosure is not limited to particular materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise.

As used herein, the following terms have the meanings ascribed to them unless specified otherwise. In this disclosure, "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law and the term is open-ended, allowing for the presence of more than that which is recited so long as basic or novel characteristics of that which is recited is not changed by the presence of more than that which is recited, but excludes prior art embodiments.

General Discussion

In accordance with the purpose(s) of the present disclosure, as embodied and broadly described herein, embodiments of the present disclosure, in some aspects, relate to intraoral vertical ramus osteotomy (IVRO) surgical guides and methods for performing intraoral vertical ramus osteotomy.

The present disclosure includes an intraoral vertical ramus osteotomy (IVRO) surgical guide (also referred to as a device) that can include a curvilinear shaft comprising a hooked distal end and a cutting guide. The device also includes a slidable component that slidably engages with the curvilinear shaft proximal to the cutting guide. The slidable component can include a curved claw. The device forms a clamp at the mid-waist of the mandibular ramus to allow for accurate placement of a trial cut for osteotomy. Advantageously, the curvilinear shaft is anatomically designed to accommodate the natural curvature of the posterior and lateral mandibular rami.

The IVRO surgical guides provided herein use the mid-posterior and mid-anterior ramus instead of the anti-lingular prominence as anatomical landmarks to guide the orientation of the osteotomy. The cutting guide includes a slot that can accommodate a saw to make a trial cut for the osteotomy. In some embodiments, the cutting guide and slot are perpendicular to the longitudinal axis of the curvilinear shaft. In other embodiments, the cutting guide can be at another angle relative to the curvilinear shaft. In various embodiments, the slot can be linear or curved (e.g. c-shaped). In some embodiments, the cutting guide can be latitudinally centered on the curvilinear shaft, while in other embodiments the cutting guide is latitudinally offset from the curvilinear shaft. The slot in the cutting guide can be open-ended or closed. In embodiments in which the cutting guide is latitudinally centered on the curvilinear shaft, the device can be reversed for use on left or right mandibular rami simply by flipping the device over. In other embodiments, the device can be designed specifically for use on either a left or right ramus.

In some embodiments, the curvilinear shaft can include measurement markings between the cutting guide and the slidable component to facilitate intraoperative measurement of the distance between the mid-anterior ramus to the osteotomy cut.

The curvilinear shaft can include a slot or track along which the slidable component moves to engage with the mid-anterior mandibular ramus. In some embodiments, the device can include a locking mechanism to lock the slidable component in place at a desired position along the curvilinear shaft. Locking mechanism can be such as a thumb screw, set screw, butterfly nut, or the like. In some embodiments, the locking mechanism could be such as a ratchet, spring clamp, cam clamp or clutch clamp.

In some embodiments, the distance between the center axis of the cutting guide and the interior edge of the hooked distal end is about 7 mm to 12 mm, about 7 to 10 mm, or about 8 mm. A device having cutting guide at a specific distance from the distal end can be selected such that the cut can be placed at a predetermined location from the posterior ramus based on the needs of a patient. In some embodiments the distance between the cutting guide and the hooked distal end can be adjusted by means of a sliding mechanism.

Traditionally, the user (e.g. a surgeon) holds a ramus measuring instrument in place to engage the mid-posterior ramus. The position of the IVRO trial cut as indicated by the ramus measuring instrument is visualized using a laryngeal mirror. The user keeps a visual memory of the approximate location of the trial cut. The ramus measuring instrument is then removed before the trial cut is made using an oscillating saw. After the initial trial cut has been made, the ramus measuring instrument is re-inserted to verify the correct placement of the trial cut. If the initial trial cut is incorrectly placed, this process is repeated until a correct trial osteotomy is achieved. In this manner, the measuring instrument is removed for the saw to be used, introducing potential error. Advantageously, because of the clamping capability of the device described herein, the user (e.g. a surgeon) can hold the IVRO surgical guide in place with one hand while using the contralateral hand to place a 11.7×7-mm oscillating saw blade in the cutting slot to initiate the trial osteotomy.

The intraoral vertical ramus osteotomy (IVRO) is a relatively simple, but useful technique with many applications, including management of horizontal mandibular excess, mandibular asymmetry and correction of minor mandibular deficiency. Modified condylotomy is a variation of the IVRO with partial stripping of the medial pterygoid attachment from the proximal segment to achieve the desired condylar sag and increased jaw joint space. Increasing joint space frequently promotes disc reduction in joints with articular disc displacement with reduction or recent progression to disc displacement without reduction; improves pain even if disc position remains unchanged; and seems to favorably alter the natural course of internal derangement.

Some of the intraoperative challenges associated with IVRO include limited visualization and difficulty judging the position of the lingua. The proposed invention addresses three problems related to poor osteotomy that leads to: 1) inadequate proximal segment medial pterygoid attachment, 2) inferior alveolar nerve damage and 3) vascular injury of the inferior alveolar, masseteric, maxillary arteries or retromandibular vein.

Early IVRO techniques, which did not emphasize preservation of proximal segment medial pterygoid attachment, were associated with a 14% incidence of open bite after maxillomandibular fixation release. IVRO techniques, which preserve medial pterygoid attachment, limit this complication.

Location of the mandibular foramen must be appreciated to avoid inferior alveolar nerve damage. Historically, the anatomical landmark for this procedure was the antilingular prominence. However, studies have proven this landmark to have poor correlation with the actual position of the lingula. In an anatomical study by Langston and Tebo, the antilingular prominence was found anterior to the mandibular foramen in 66% of the adult mandibular specimens. These difficulties are associated with up to 8.82% incidence of long-term neurosensory deficit affecting the inferior alveolar nerve after IVRO.

Poor IVRO osteotomy design can lead to injuries to the vasculatures located in the medial and/or posterior aspect of the ramus resulting in active bleeding that can be difficult to control. A properly positioned osteotomy cut would limit this complication. Although IVRO has many advantages over sagittal split osteotomy, it has not been widely used by most surgeons. Some of the intraoperative challenges associated with IVRO include limited visualization and difficulty judging the position of the lingua. Complications of technique include poor osteotomy cut that leads to inadequate proximal segment medial pterygoid attachment, inferior alveolar nerve damage and vascular injury of the inferior alveolar, masseteric, or maxillary arteries.

Several methods have been suggested to improve the accuracy of the IVRO cut and to avoid neurovascular damage including the use of stereolithographic cutting guide, ramus measuring device, elastic thread connected to two sigmoid retractors as the cutting guide, endoscopy with a piezoelectric osteotome, and navigation assisted surgery. These methods, however, are not without drawbacks. Navigation assisted IVRO, for example, requires a preoperative CT scan taken with several mandibular bone screws in place. Intraoperatively, Kirschner wires are inserted in the mandibular menton region for attachment of the reference frame. The bone screws function as the reference points during the registration process. The registration and calibration of the surgical device add to the operation time. The navigation equipment can be cumbersome to use and the equipment itself is expensive.

To address the challenges associated with the vertical ramus osteotomy, a multidisciplinary team was assembled, and an anatomical study of the mandibular ramus based on full-field cone beam CT images of fifty patients (100 rami) underwent orthognathic surgery at VUMC was conducted. By combining the advantages of 3D Models (3DM) and Rapid Prototyping (RP) technologies and the data collected from this anatomical study, various prototypes of IVRO surgical cutting guides were designed as described herein.

Advantageously, the IVRO surgical guide described herein enables the user to make the vertical ramus osteotomy with the desired angulation and distance from the posterior border of the ramus to preserve proximal segment medial pterygoid attachment and avoid injury to the inferior alveolar neurovascular bundle.

Provided herein is an anatomically designed IVRO surgical guide (also referred to as the device) that engages both the mid-posterior and mid-anterior aspects of the ramus, leading to a more accurately positioned trial osteotomy cut. The mid-posterior ramus is defined as the most concave point along the posterior ramus. The mid-anterior ramus is defined as the most concave point along the anterior ascending ramus.

After subperiosteal dissection with exposure of the lateral aspect of the ramus from the inferior border of the ramus to the sigmoid notch, sufficient temporalis tendon is stripped from the anterior border and lateral aspect of the coronoid process to release tension in the buccal flap. A Bauer retractor is placed to protect the contents of the sigmoid notch. The distal tip of the device is adapted to the mid-posterior ramus. If the distal tip is not well adapted to the posterior border, the osteotomy will likely be placed too far posteriorly. A well-adapted IVRO surgical guide allows the user to position the guide using one hand with good stability. The devices provided herein include a hooked distal end to contour well to the posterior border.

With the device correctly positioned, the cutting slot facilitates the trial vertical osteotomy at the desired distance from the posterior ramus starting at the mid-portion of the ramus. The vertical osteotomy is typically made with a 11.7×7-mm oscillating saw blade. Once the position of the trial osteotomy has been confirmed to be satisfactory, the surgical guide is removed. The trial cut is then extended through the medial cortex of the ramus. The osteotomy is carried superiorly to the sigmoid notch and completed inferiorly towards the inferior border of the ramus.

In some embodiments, the IVRO surgical guide may be made from material suitable for autoclaving, including but not limited to surgical grade metals such as stainless steel, titanium, tantalum, platinum, palladium, or surgical grade metal alloys that are corrosion- and stain-resistant. In other embodiments, the IVRO surgical guide may be manufactured from a biocompatible material using additive manufacturing. In some embodiments, one or more parts (including but not limited to the slidable component and the handle) may be disposable.

In some embodiments, the IVRO surgical guide can be customized to a specific mandible using 3D imaging and rapid prototyping.

In some embodiments, a device can be selected that has a desired placement of the cutting guide based on preoperative or perioperative imaging.

Examples

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

For clarity, directional terms used herein to describe the device refer to the device when placed on a patient and from the user's perspective. For example, the top of the device is the superior portion when placed on a patient's mandibular ramus, and the front of the device is the portion facing the user when viewing the lateral side of the ramus. Several advantageous features of the surgical guide (e.g. the device) include the curvilinear design of the shaft that allows accurate adaptation of the distal curved tip around the mid-posterior ramus, the curved claw on a sliding component along the shaft that engages the mid-anterior ramus, and the millimeter markings on the shaft to allow intraoperative measurement of the A-P distance between one or both rami and the osteotomy cut.

The locations of the mid-anterior ramus and mid-posterior ramus can be determined through imaging, such as via preoperative panorex x-ray or cone beam CT. A horizontal line connecting the mid-anterior and mid-posterior ramus is the mid-waistline of the ramus. The goal of the IVRO procedure is to perform a full-thickness vertical osteotomy through the mandibular ramus posterior to the mandibular foramen with the creation of a proximal segment consisting of the condyle and posterior ramus and a distal segment containing the anterior ramus, coronoid process, inferior alveolar nerve, and tooth-bearing mandible. When the IVRO is made perpendicular to the mid-waistline of the ramus and about 7-12 mm from the posterior ramus, an IVRO with adequate proximal segment and medial pterygoid attachment while avoiding neurosensory and vascular injuries can be achieved with high consistency.

During preoperative surgical planning, data regarding the locations of the mid-anterior and mid-posterior ramus, dimensions of the mandibular ramus, location of the mandibular foramen, the safe distance between the posterior ramus to the IVRO cut can be determined based on preoperative radiographs. When the device is positioned correctly along the mid-waistline of the ramus, the intraoperative measurement of the distance between the mid-anterior ramus and the osteotomy cut should closely approximate the preoperative measurement. Visual inspection and confirmation of the correct positioning of the device can be achieved by using a laryngeal mirror or a 30° endoscope.

Figure 1F:
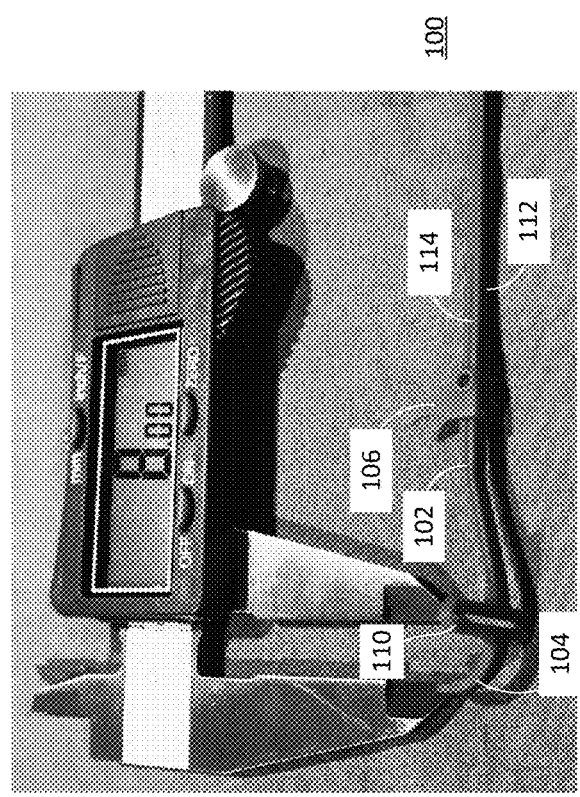

With reference now to FIGS. 1A-1F, an embodiment of the device 100 from various views is shown. FIGS. 1A and 1B present a top and front view of an embodiment of the IVRO surgical guide, respectively. Due to the medial rotation of the posterior ramus and curvature of the lateral ramus, a curvilinear shaft 102 is designed to allow the device to engage both the anterior and posterior mid-ramus points. One end of the curvilinear shaft 102 ends in a hook 104 that engages with the posterior ramus. A handle 112 is at the other end of curvilinear shaft 102. An adjustable sliding component 106 slidably engages with curvilinear shaft 102 along slot 114. The adjustable sliding component 106 has a curved claw 108 to engage with the mid-anterior ramus. The curvilinear shaft 102 also includes a cutting guide 110 that serves as a guide for a saw and allows for placement of a trial cut for osteotomy. FIGS. 1C and 1D illustrate movement of the adjustable sliding component 106 from a perspective view. In some embodiments, the curvilinear shaft 102 can have measurement markings (not shown) between the adjustable sliding component 106 and the cutting guide 110. FIG. 1E presents various views of the sliding component (left side perspective, front, and right side respectively). The distance between the interior edge of the hook and the center axis of the cutting guide 110 determines the distance of the osteotomy trial cut from the posterior ramus. FIG. 1F presents a prototype of the IVRO surgical guide with the cutting guide 110 located 8 mm (shown on calipers) from the interior of hook 104; in this example, an osteotomy cut made using the cutting guide 110 would be located 8 mm from the posterior ramus.

The adjustable sliding component 106 is designed to wrap around and slide along the curvilinear shaft 102 of the surgical guide. The location of the mid-anterior ramus and its distance from the occlusal plane can be measured on preoperative radiographs. Once the mid-anterior ramus is identified intraoperatively, its location can be marked with a sterile pencil. The curved claw 108 on the sliding component 106 is designed to engage the mid-anterior ramus. In some embodiments, sliding component 106 includes a screw 107 or other locking mechanism to engage with the curvilinear shaft 102, which enables the user to fasten the curved claw 108 around the mid-anterior ramus and lock the sliding component 106 into place. The device can be used on either the left or right mandibular ramus of a patient simply by flipping it over.

With the hook 104 at the distal tip well-adapted to the posterior border of the patient's ramus and the curved claw 108 of the sliding component 106 secured around the mid-anterior ramus, the shaft of the surgical guide is thereby positioned along the mid-waistline of the ramus. In the shown embodiment, the cutting guide 110 is positioned perpendicular to the shaft to provide a vertical cut, although other angles or shapes of the cutting guide can be envisioned by one of ordinary skill in the art. In the shown embodiment, the total length of the vertical cutting slot is 18 mm. This accommodates the cutting surface of the 11.7 mm×7-mm fan-shaped oscillating saw blade (for example, FIGS. 2C and 3C).

In this particular embodiment, the cutting guide 110 is positioned 8 mm anterior to the posterior border of the mandible. When treatment planning a mandibular setback using IVROs, the greater the mandibular setback planned, the wider the proximal segment needs to be to maintain sufficient medial pterygoid muscle attachment. In some embodiments, IVRO surgical guides 100 can be provided with the cutting slots positioned at 1 mm intervals from 7 mm to 12 mm anterior to the posterior border of the mandible to facilitate osteotomy cuts with the desired proximal segment widths. The devices can be provided individually or as a set to accommodate various needs.

In some embodiments, handle 112 can be integral to the device, such that the hook 104, curvilinear shaft 102, and handle 112 are formed from a single piece. In other embodiments, handle 112 can be formed as a separate piece and can be detachable and/or formed from a different material.

Figure 2B:
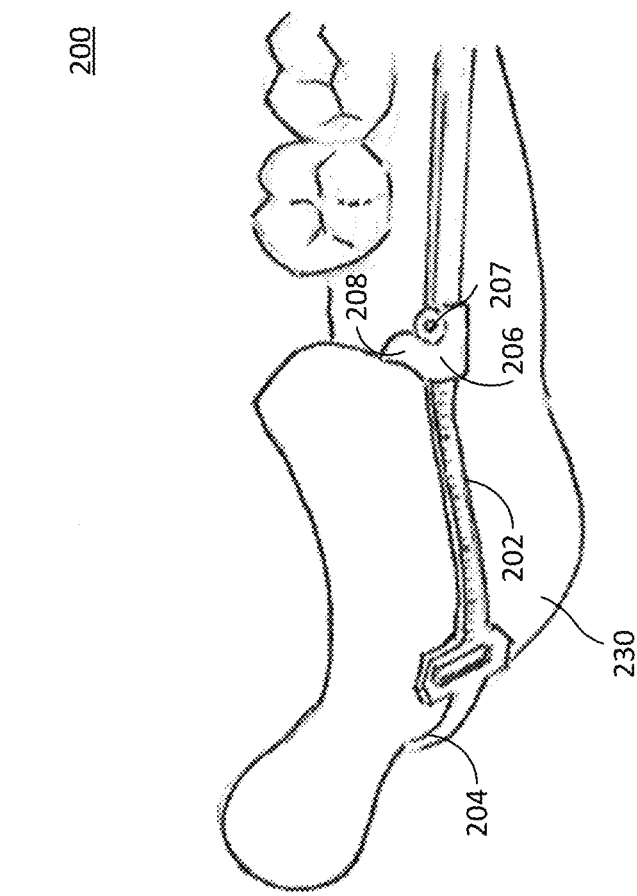
FIG. 2B provides a top perspective view of the surgical guide shown in FIG. 2A on a right mandibular ramus.
Figure 2A:
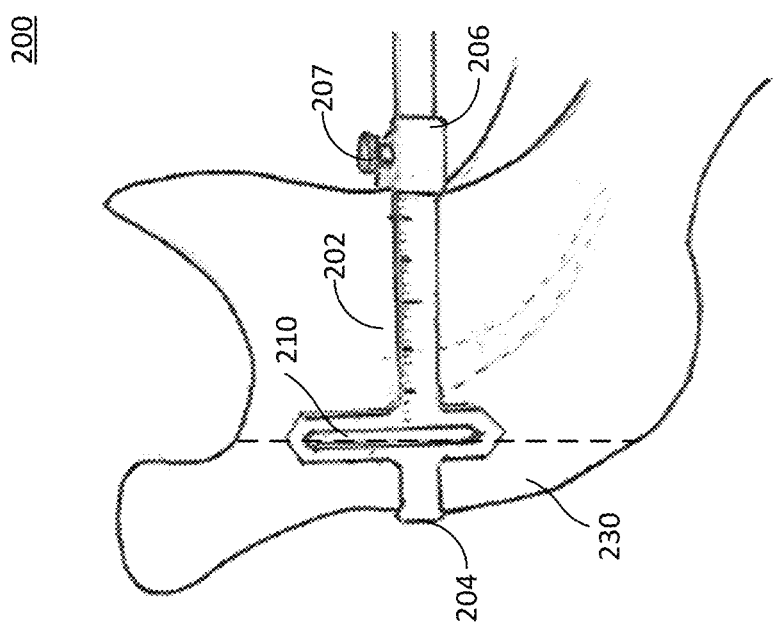
FIG. 2A provides a lateral view of an IVRO surgical guide on a right mandibular ramus with the distal tip engaging the mid-posterior ramus and the curved claw of the sliding component engaging the mid-anterior ramus in accordance with embodiments of the present disclosure.
Figure 2C:
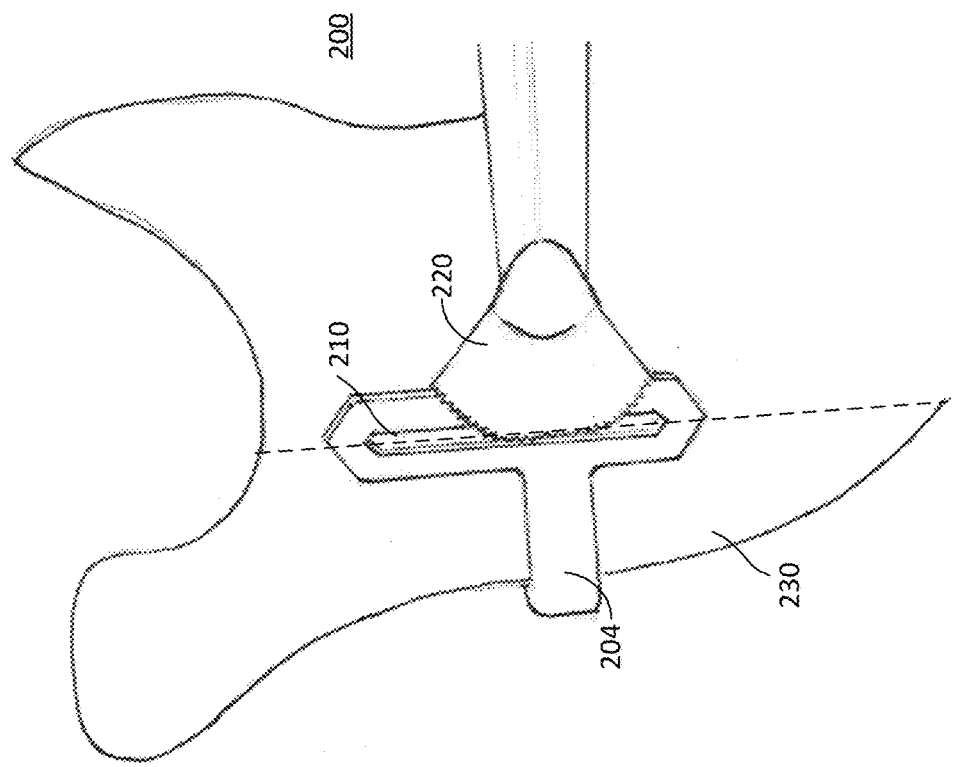
FIG. 2C provides a lateral view of the IVRO surgical guide where the surgical guide is secured around a right mandibular ramus and an oscillating saw blade is placed in the cutting slot to initiate the trial osteotomy cut.

FIG. 2A provides a lateral view of device (an IVRO surgical guide) 200 on a right mandibular ramus with the distal tip engaging the mid-posterior ramus and the curved claw 208 of the sliding component 206 engaging the mid-anterior ramus in accordance with embodiments of the present disclosure. A dashed line represents the desired osteotomy location. Measurement markings are shown on the curvilinear shaft 202. FIG. 2B provides a top perspective view of the surgical guide shown in FIG. 2A on a right mandibular ramus 230. In this view, the shape of the curvilinear shaft 202, which follows the anatomical curvature of the human mandibular ramus, is readily demonstrated. FIG. 2C provides a lateral view of the device 200 where the surgical guide is secured around a right mandibular ramus and an oscillating saw blade 220 is placed in the cutting guide 210 to initiate the trial osteotomy cut.

In some embodiments, the vertical cutting guide 210 is not centered on the curvilinear shaft 202 but is offset latitudinally. In other words, a greater portion of the cutting guide is positioned on one side of the shaft than the other. In this particular example, the cutting guide 210 is positioned across the shaft with 4 mm below the shaft and the remaining 14 mm of the cutting slot across the shaft and above the shaft, when above and below refers to the shaft's longitudinal axis. This design allows adaptation of the cutting slot to the concavity of the ramus superior to the anti-lingula. It also facilitates the osteotomy to continue superiorly towards the sigmoid notch after the trial osteotomy. The triangularly shaped superior and inferior ends of the cutting slot also provide visual aids to assist the users in correct positioning of the surgical guide and directing the trial osteotomy with the desired angulation. The millimeter ruler on the shaft allows the user to measure the distance between the cutting slot and the mid-anterior ramus. This intraoperative measurement serves as an additional verification of proper positioning of the surgical guide. In embodiments having an offset curvilinear shaft 202, the device 200 can be provided in versions for a left ramus and a right ramus.

Figure 3C:
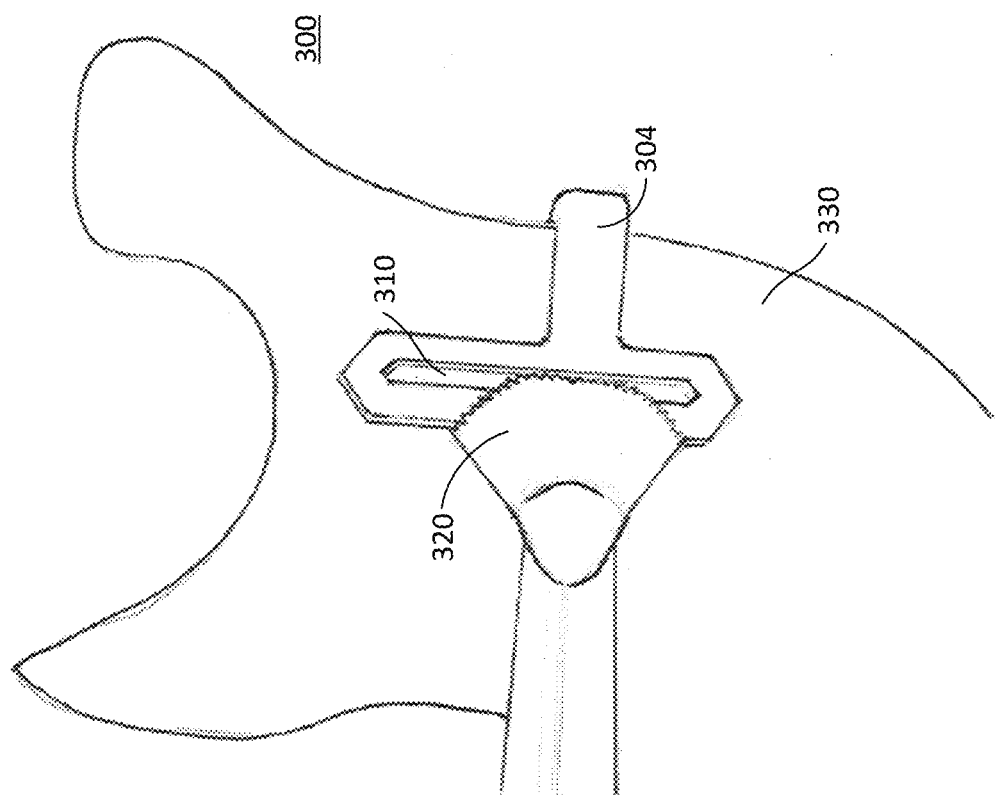
FIG. 3C provides a lateral view of the IVRO surgical guide where the surgical guide is secured around a left mandibular ramus and an oscillating saw blade is placed in the cutting slot to initiate the trial osteotomy cut.

FIG. 3A provides a lateral view of an example IVRO surgical guide device 300 on a left mandibular ramus 330 with the distal tip engaging the mid-posterior ramus and the curved claw of the sliding component engaging the mid-anterior ramus. FIG. 3B provides a top perspective view of the device 300 on a left mandibular ramus 330. FIG. 3C shows the device 300 secured around a left mandibular ramus with an oscillating saw blade 320 placed in the cutting guide 310 to initiate the trial osteotomy cut. Device 300 has a cutting guide 310 that is not latitudinally centered on curvilinear shaft 302, as described in reference to FIGS. 2A-2C.

Figure 4A:
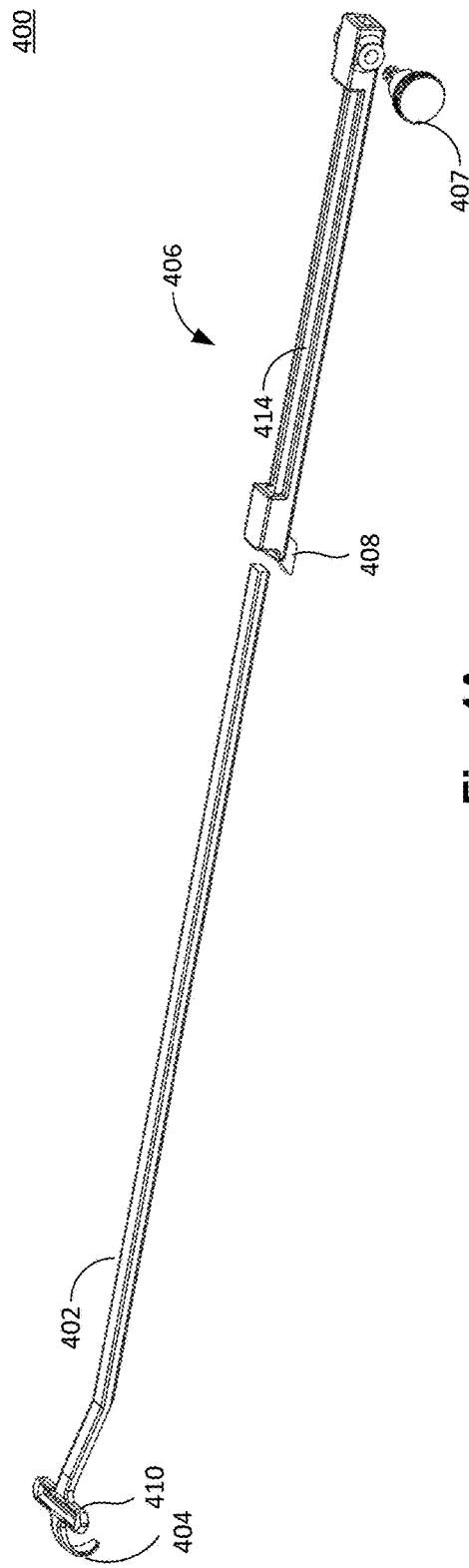
Figure 4B:
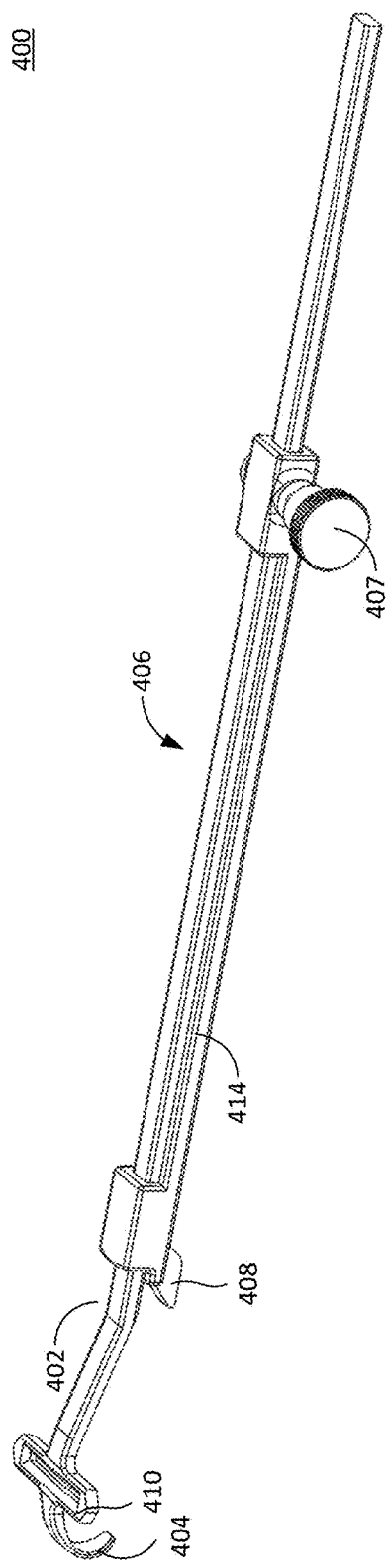
Figure 4C:
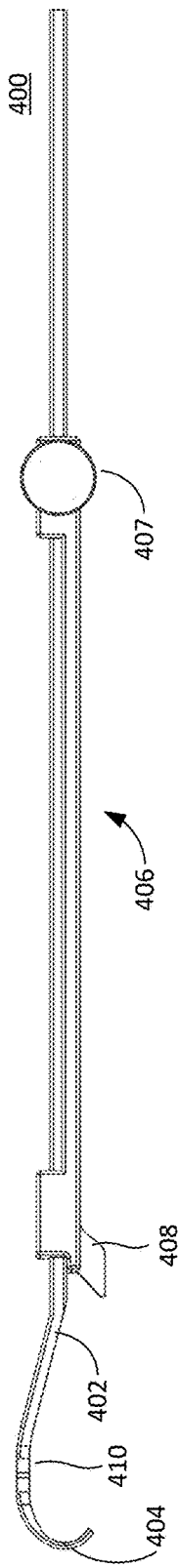
Figure 4D:
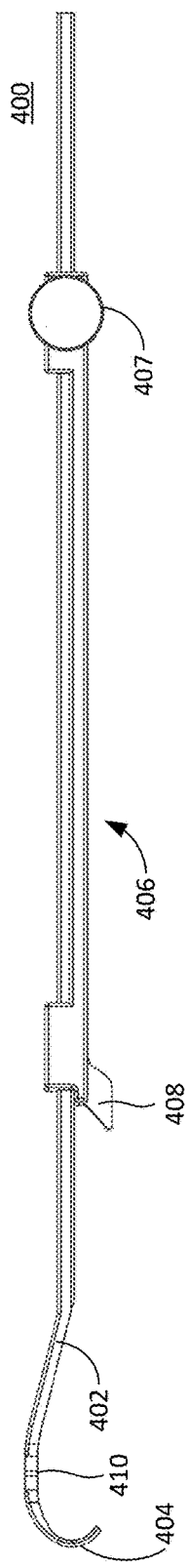
Figure 4E:
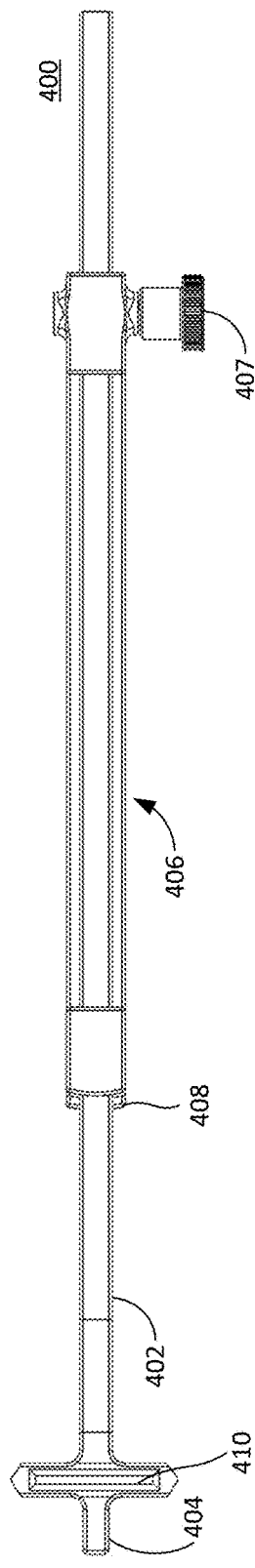

FIGS. 4A-4H provide various views of device 400 having the curved claw 408 as part of the handle, and wherein the handle slides to adjust the device 400 to the patient. In this example, the sliding component 406 functions as the handle. Sliding component 406 includes the curved claw 408 at the distal end and a locking means 407 at the proximal end. Curvilinear shaft 402 slidably engages with a slot 114 in sliding component 406 such that sliding component 406 can be adjusted to engage the mid-anterior ramus. In some embodiments, slot 114 can be a track. Locking means 407 can be used to hold the sliding component 406 in place. Locking means 407 can be such as a set screw or thumb screw (shown) or other locking means as can be envisioned by one of ordinary skill in the art. FIG. 4A provides an exploded perspective view of device 400 with a curved claw and set screw adapted to the handle. FIG. 4B provides an assembled perspective view of device 400. FIG. 4C shows a front perspective view in which the device 400 is in a closed position to engage the ramus (e.g. sliding component 406 has been directed toward the distal end such that ramus can be clamped between curved claw 408 and hook 404). FIG. 4D shows device 400 in an open position in which the sliding component 406 is directed away from the distal end such that the ramus would not be gripped by the device 400. FIG. 4E is a top view of the device in the position shown in FIG. 4D. FIGS. 4F-4H provide various views of the sliding component 406. An arrow in FIG. 4G indicates a curved area that can be matched to the most concave point of anterior ascending ramus to aid the user in placing the device and to avoid creating a stress concentration. In the example shown in FIGS. 4A-4H, the cutting guide 410 is latitudinally centered on the curvilinear shaft 402 such that the device can be used interchangeably for a left- or right-side procedure. Although not shown, measurement markings can be included on the curvilinear shaft.

FIGS. 5A-5D provide an example of a device 500 in which the cutting guide 510 is open-ended. This example is configured similarly to that shown in FIGS. 1A-F, where the sliding component 506 slides along slot 114 on curvilinear shaft 502 and handle 512 is fixed. However, as can be appreciated, the open-ended cutting guide 510 could be included in a version of the device such as the one described in FIGS. 4A-4H where sliding component 406 is integrated in the handle. FIG. 5A presents a top view; FIG. 5B presents a front view; FIGS. 5C and 5D illustrate the adjustable sliding component 506 from a perspective view. Cutting guide 510 is shown with a greater proportion above the curvilinear shaft 502 (e.g. offset), but can be positioned centrally on the curvilinear shaft 502 or with a greater proportion below the curvilinear shaft 502 as can be envisioned by one of ordinary skill in the art. As mentioned above, although not shown, measurement markings can be included on curvilinear shaft 502.

Figure 6A:
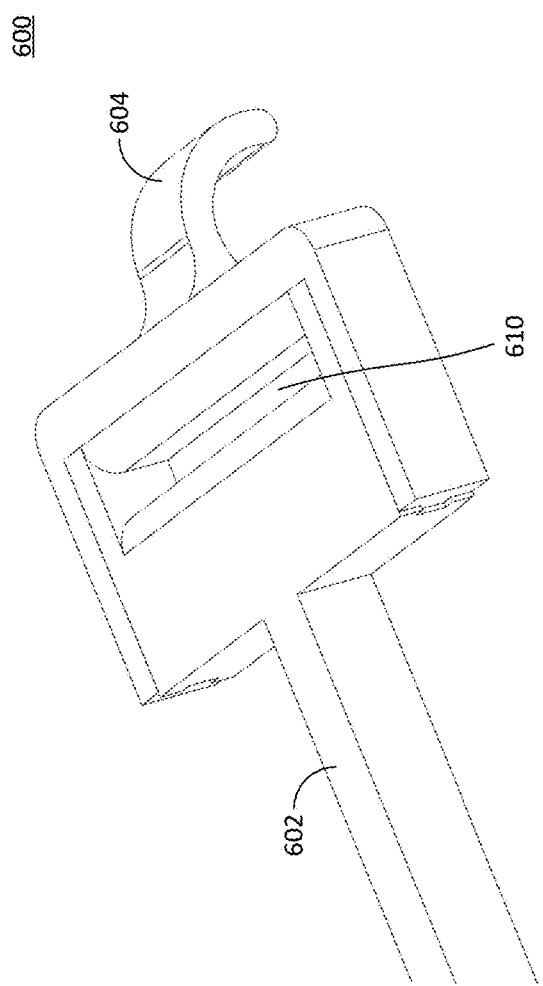
FIGS. 6A-6B illustrate a cutting slot with adjustable positioning in accordance with embodiments of the present disclosure.
Figure 6B:
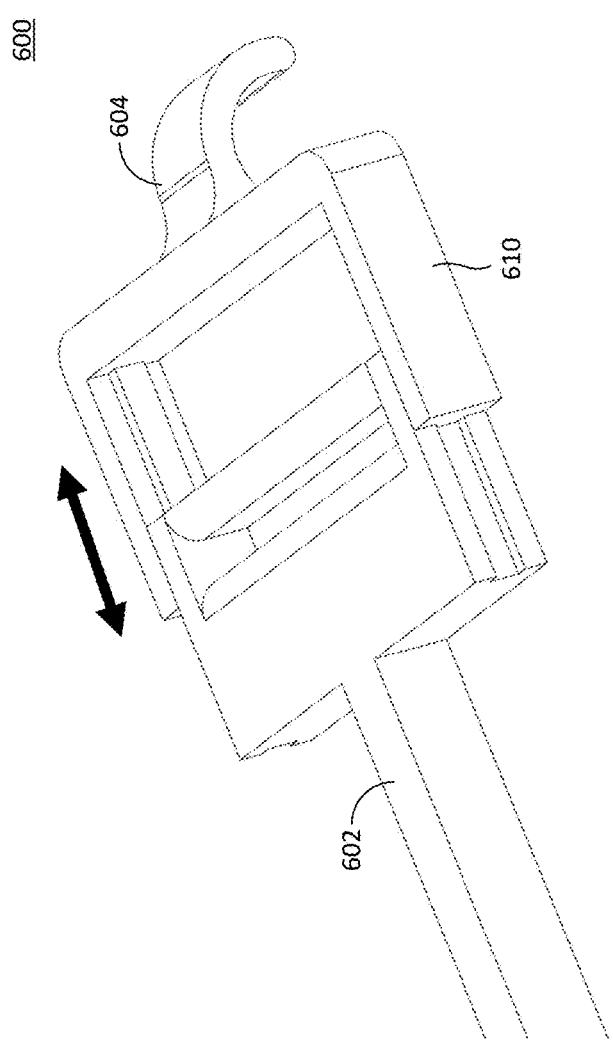

FIGS. 6A-6B provide an example of an alternative configuration which enables an adjustable distance between cutting guide 610 and hook 604. This configuration could be used with any of the examples described above in FIGS. 1A-4H. Cutting guide 610 is integrated into curvilinear shaft 602, and hook 604 slidably engages along the outside of cutting guide 610 such that when hook 604 is fitted to the mid-posterior ramus, the distance between the cutting guide 610 and the hook 604 can be adjusted to make the trial osteotomy cut in a desired position. In some embodiments the distance can be from about 6 mm in the closed position to about 12 mm in the fully open position. FIG. 6A shows the cutting slot in the default (closed) position. FIG. 6B shows the sliding mechanism in the open position, allowing for the location of the cutting slot 610 to be positioned by the surgeon in relation to the posterior ramus. In some embodiments, the sliding mechanism can include spaced teeth such that the distance between the hook 604 and the cutting guide 610 can be set at predetermined intervals (e.g. 1 mm). In other embodiments the sliding mechanism can include a locking means.

Figure 7A:
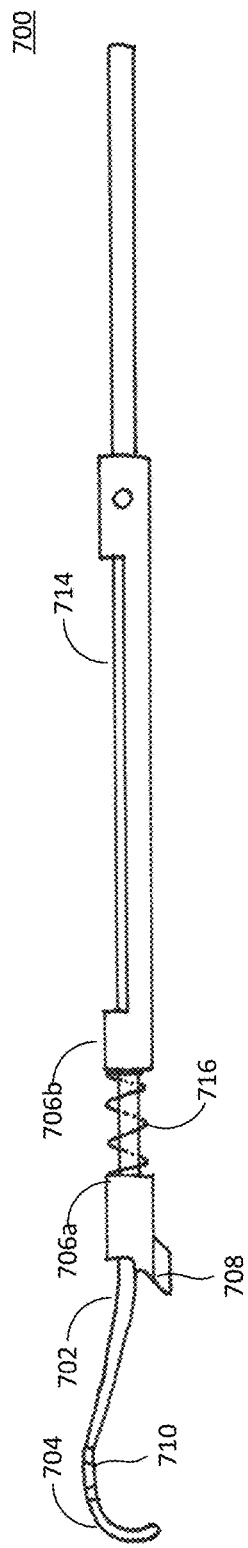
FIGS. 7A-7C provide an IVRO surgical guide having an adjustable clamping means in accordance with embodiments of the present disclosure.
Figure 7B:
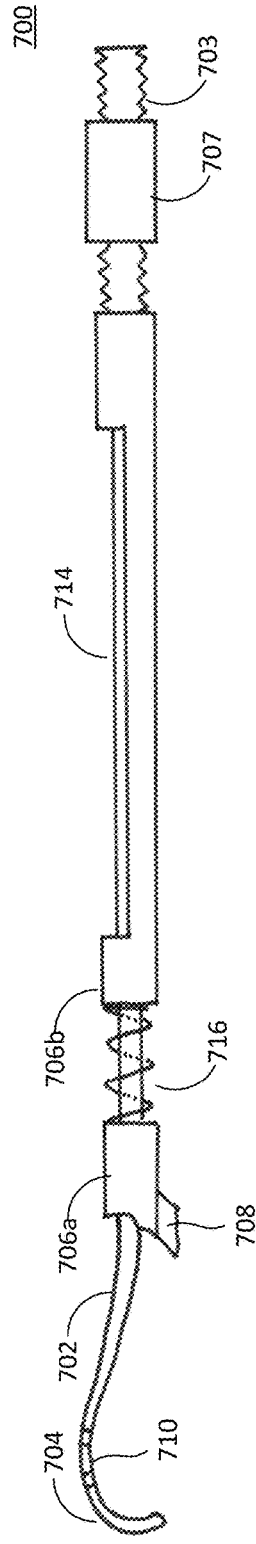
Figure 7C:
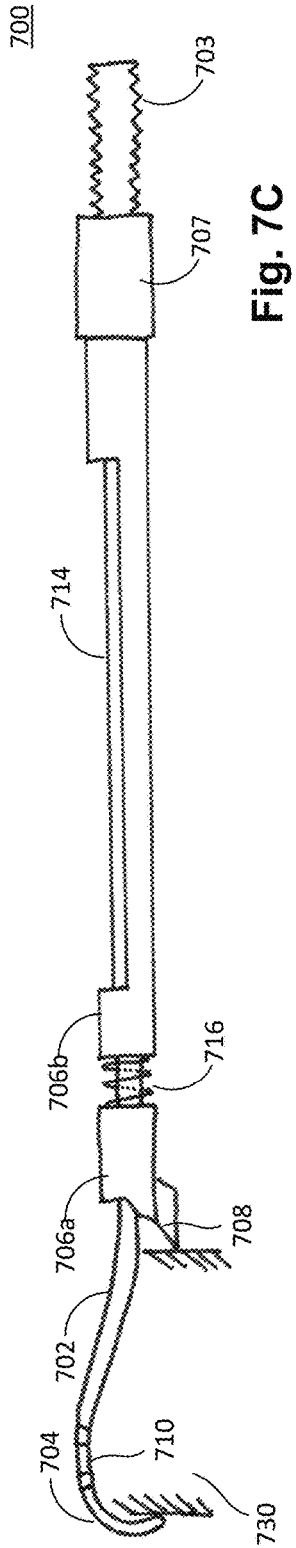

FIGS. 7A-7C provide an example of the device 700 having an alternative method for adjusting the sliding component position and the resulting clamping pressure. In this example, a spring is placed in series to prevent overloading of the clamp on the bone. This configuration provides adjustable clamping pressure that enables the operator to adjust the position and orientation of the device before fully clamping it in place. The sliding component comprises two pieces 706a and 706b connected by spring 716. Curved claw 708 is located on sliding component piece 706a. When the threaded knob (or nut 707) at the rear of the device is twisted in one direction it engages the rear piece of the sliding component (706b) and pushes it forward and compresses the spring 716, thereby increasing the clamping pressure on the bone. When the nut 707 is twisted in the opposition direction, spring 716 relaxes and the clamp will release. Advantageously, the device is held in position by a low pitch of the threads, enabling minute adjustments of the clamping force.

FIGS. 7B and 7C show one possible means for tuning the clamping pressure. The clamping pressure is illustrated as a nut 707 screwed onto a threaded portion 703 of curvilinear shaft 702. However, other means could be substituted, including but not limited to a butterfly nut or ratchet. In some embodiments, the nut 707 could be incorporated into the handle, or part 706b could be internally threaded and function as the nut 707. Advantageously, including the spring in series can prevent overloading of the clamp on the bone, and can provide adjustable clamping pressure which enables the operator to adjust the position and orientation of the device before fully clamping the device in place.

FIGS. 8A-8B show an example of a prototype device 800 in the clamped position on a 3D-printed right mandibular ramus. As can be appreciated from the perspective view in FIG. 8A, the curvilinear shaft 802 follows the curvature of the ramus. The curvilinear shaft 802 ends in a hook 804 that holds the mid-posterior ramus. The adjustable sliding component 806 has been slid along slot 814 to clamp the device 800 into place such that curved claw 808 is hooked around the mid-anterior ramus. Sliding component 806 includes a locking mechanism 107 (shown here as a screw) to lock the sliding component 806 into place. The curvilinear shaft 802 also includes a cutting guide 810 that serves as a guide for a saw and allows for placement of a trial cut for osteotomy. In the shown embodiment, the cutting guide 810 is positioned perpendicular to the shaft to provide a vertical cut, although other angles or shapes of the cutting guide can be envisioned by one of ordinary skill in the art. In this particular embodiment, the cutting guide 810 is positioned 8 mm anterior to the posterior border of the mandible.

Although embodiments have been described herein in detail, the descriptions are by way of example. The features of the embodiments described herein are representative and, in alternative embodiments, certain features and elements may be added or omitted. Additionally, modifications to aspects of the embodiments described herein may be made by those skilled in the art without departing from the spirit and scope of the present invention defined in the following claims, the scope of which are to be accorded the broadest interpretation so as to encompass modifications and equivalent structures.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

It should be noted that measurements, amounts, and other numerical data can be expressed herein in a range format. It is also understood that there are a number of values disclosed herein, and that each value is also herein disclosed as "approximately" that particular value in addition to the value itself. For example, if the value "10" is disclosed, then "approximately 10" is also disclosed. Similarly, when values are expressed as approximations, by use of the antecedent "approximately," it will be understood that the particular value forms a further aspect. For example, if the value "approximately 10" is disclosed, then "10" is also disclosed.

As used herein, the terms "about," "approximately," "at or about," and "substantially equal" can mean that the amount or value in question can be the exact value or a value that provides equivalent results or effects as recited in the claims or taught herein. That is, it is understood that amounts, sizes, measurements, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In general, an amount, size, measurement, parameter or other quantity or characteristic is "about," "approximate," "at or about," or "substantially equal" whether or not expressly stated to be such. It is understood that where "about," "approximately," "at or about," or "substantially equal" is used before a quantitative value, the parameter also includes the specific quantitative value itself, unless specifically stated otherwise.

Where a range is expressed, a further aspect includes from the one particular value and/or to the other particular value. Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

What is claimed is:

1. An intraoral vertical ramus osteotomy (IVRO) surgical guide comprising:
    a curvilinear shaft comprising a hooked distal end and a cutting guide, wherein a distance between a center of the cutting guide and an interior edge of the hooked distal end is about 7 mm to 12 mm and wherein the hooked distal end is slidably engaged with the cutting guide such that the distance between the center of the cutting guide and an interior edge of the hooked distal end is adjustable; and
    a slidable component slidably engaged with the curvilinear shaft proximal to the cutting guide, wherein the slidable component comprises a curved claw.

2. The IVRO surgical guide of claim 1, wherein the slidable component comprises a first piece connected to a second piece by a spring, and wherein a pressure applied to the second piece compresses the second piece to apply adjustable clamping pressure on the ramus.

3. The IVRO surgical guide of claim 2, wherein the pressure is applied by twisting a knob or nut.

4. The IVRO surgical guide of claim 1, wherein the curvilinear shaft further comprises measurement markings between the cutting guide and the slidable component.

5. The IVRO surgical guide of claim 1, wherein the curvilinear shaft further comprises a slot along which the slidable component engages with the curvilinear shaft.

6. The IVRO surgical guide of claim 1, wherein the slidable component further comprises a locking mechanism to lock the slidable component in place at a desired position along the curvilinear shaft.

7. The IVRO surgical guide of claim 1, wherein the cutting guide is latitudinally centered on the curvilinear shaft.

8. The IVRO surgical guide of claim 1, wherein the cutting guide is latitudinally offset from the curvilinear shaft.

* * * * *